(12) United States Patent
Kao et al.

(10) Patent No.: US 6,399,335 B1
(45) Date of Patent: Jun. 4, 2002

(54) γ-PHOSPHOESTER NUCLEOSIDE TRIPHOSPHATES

(75) Inventors: C. Cheng Kao; Theodore Widlanski; William Vassiliou, all of Bloomington; Jeffrey Epp, Indianapolis, all of IN (US)

(73) Assignee: Advanced Research and Technology Institute, Inc., Indianapolis, IN (US)

( * ) Notice: Subject to any disclaimer, the term of this patent is extended or adjusted under 35 U.S.C. 154(b) by 0 days.

(21) Appl. No.: 09/441,108

(22) Filed: Nov. 16, 1999

(51) Int. Cl.[7] ............ C12Q 1/68; C12P 19/34; C07H 19/00; C07H 21/00; C07H 21/02
(52) U.S. Cl. ............ 435/91.1; 435/6; 435/91.2; 536/22.1; 536/23.1; 536/25.3
(58) Field of Search .......... 435/6, 91.1, 91.2; 536/22.1, 23.1, 25.3

(56) References Cited

U.S. PATENT DOCUMENTS 5,187,085 A * 2/1993 Lee et al. ............ 435/91
5,260,433 A * 11/1993 Engelhardt et al. ........ 536/23.1

OTHER PUBLICATIONS

Liu et al. "Synthesis of three novel supercharged –methylene analogues of adenosine triphosphate" Chem. Commun. pp. 87–88, 1997*

* cited by examiner

Primary Examiner—Jezia Riley
(74) Attorney, Agent, or Firm—Richard Aron Osman

(57) ABSTRACT

The invention provides methods and compositions for polymerizing a particular nucleotide with a polymerase. In general, the method involves (a) forming a mixture of a polymerase and a nucleoside triphosphate (NTP) comprising α, β and γ phosphates and a γ-phosphate phosphoester-linked functional group; and incubating the mixture under conditions wherein the polymerase catalyzes cleavage of the NTP between the α and β phosphates, liberating a pyrophosphate comprising the functional group and polymerizing the resultant nucleoside monophosphate, i.e. incorporates the nucleoside monophosphate in a nascent polynucleotide. A variety of functional groups compatible with the polymerization reaction are provided.

23 Claims, No Drawings

γ-PHOSPHOESTER NUCLEOSIDE TRIPHOSPHATES

The research described in this application was supported in part by USDA grant 9702126 and NIH Postdoctoral Fellowship 1 F32 CA77883-01A1. The U.S. government may have rights in any patent issuing on this application.

FIELD OF THE INVENTION

The field of the invention is the use of γ-phosphoester nucleoside triphosphates in polymerase reactions.

BACKGROUND OF THE INVENTION

The human immunodeficiency virus infects over 40 million people worldwide and the Hepatitis C virus has infected approximately 2% of the world's population. The economic and medical impacts of such emerging epidemics demonstrate clearly the need to rapidly and effectively assess the efficacy of viral inhibitors. Assaying inhibitors of viral RNA or DNA synthesis is a time consuming and costly process that often requires radioisotopes. This screening process is expensive, time consuming, and requires special handling due to the use of radioisotopes. Previous attempts to make colorimetric or fluorescent nucleotide analogs useful for the detection of polymerase activity primarily employ a detectable chromophore or fluorophore attached to the base or ribose portion of a nucleotide. The signal is then incorporated into the newly formed product nucleic acid, hence necessitating an often lengthy and labor-intensive step to separate the products from the reactants.

Several companies sell products that incorporate a detectable reagent into the product of polymerase synthesis, including Boehringer (Genius kit), Life Technologies INC., GIBC/BRL, Sigma (biotinylated nucleotides, fluorescent nucleotides), Molecular Probes Inc. (a large range of fluorescent and caged nucleotides), Li-Cor (dyes attached to DNAs for DNA sequencing), etc. Reports of γ-phosphoesters of nucleoside triphosphates have described them as non-hydrolyzable and used them in solid phase affinity purification protocols, e.g. Clare M. M. Haystead, et al., Gamma-phosphate-linked ATP-Sepharose for the affinity purification of protein kinases, Eur. J. Biochem. 214, 459–467 (1993), esp. p.460, col. 2, line 23. We synthesized large numbers of γ-phosphoester nucleoside triphosphates and found that while they are indeed non-hydrolyzable by many enzymes, they are often suitable substrates for RNA and DNA polymerases.

SUMMARY OF THE INVENTION

The invention provides methods and compositions for polymerizing a particular nucleotide with a polymerase. In general, the method involves (a) forming a mixture of a polymerase and a nucleoside triphosphate (NTP) comprising α, β and γ phosphates and a γ-phosphate phosphoester-linked functional group; and (b) incubating the mixture under conditions wherein the polymerase catalyzes cleavage of the NTP between the α and β phosphates, liberating a pyrophosphate comprising the functional group and polymerizing the resultant nucleoside monophosphate. i.e. incorporates the nucleoside monophosphate in a nascent polynucleotide.

A variety of functional groups compatible with the polymerization reaction are provided. In one embodiment, the functional group is a detectable label and the method further comprises the step of detecting the label, wherein a wide variety of chromogenic and luminogenic labels are provided.

In another embodiment, the functional group is a cell delivery enhancing moiety, —OR, wherein R is independently selected from: substituted or unsubstituted (C1–C18) alkyl, alkenyl, alkynyl and aryl, each inclusive of carbocyclic and heterocyclic. These substituents provide enhanced therapeutic availability through enhanced gut or blood stability, cellular and/or membrane permeability, host phosphatase stability, etc. This aspect provides a wide variety of generally membrane permeable, relatively hydrophobic R substituents.

In another embodiment, the functional group is a polymerase specificity enhancing moiety, —OR, wherein R is independently selected from: substituted or unsubstituted (C1–C18) alkyl, alkenyl, alkynyl and aryl, each inclusive of carbocyclic and heterocyclic. These substituents are readily identified in comparative and competitive enzyme assays.

DETAILED DESCRIPTION OF SPECIFIC EMBODIMENTS OF THE INVENTION

The following descriptions of particular embodiments and examples are offered by way of illustration and not by way of limitation.

The general method involves forming a mixture of a polymerase and a nucleoside triphosphate (NTP) comprising α, β and γ phosphates and a γ-phosphate phosphoester-linked functional group; and incubating the mixture under conditions wherein the polymerase catalyzes cleavage of the NTP between the α and β phosphates, liberating a pyrophosphate comprising the functional group and polymerizing the resultant nucleoside monophosphate. The mixture generally also comprises a template, a nascent polynucleotide and other reagents which facilitate the polymerase reaction, such as salts, buffers, etc. The mixture may be formed in any context, such as in vitro, within a virus or cell, etc. Monitoring polynucleotide synthesis by continuous measurement assays can be performed with homopolymeric templates and a single labeled NTP. Alternatively, continuous monitoring of polymerase activity can be performed by synthesizing all four modified nucleotides, rendering all nucleotides resistant to alkaline phosphatase.

A wide variety of polymerases may be employed, including DNA- and/or RNA-dependent RNA polymerases and DNA- and/or RNA-dependent DNA polymerases. Depending on the application, the polymerase may reside in a cell or virus, such as within its natural host cell environment, or be isolated or in vitro, such as isolated from cellular, microbial and/or viral source material. In many cases, suitable polymerases are commercially available, e.g. Taq, a DNA-dependent DNA polymerase (Boehringer Mannheim (BM) catalog #1-146-165); Klenow fragment (BM catalog #1-008-404) reverse transcriptase (RT), e.g. Moloney murine leukemia virus RT (BM catalog #1-062-603), human immunodeficiency virus RT (BM catalog #1-465-333). Exemplary targetable pathogenic polymerases include reverse transcriptases (e.g. from HIV, and hepatitis B), viral RNA polymerases (e.g. from HCV and Dengues virus) and DNA polymerases (e.g. Herpes and Epstein-Barr virus DNA polymerases).

A wide variety of NTPs which function as substrates for the targeted polymerase may be used in the method. The nucleotide may comprise a conventional purine or pyrimidine base, such as adenine, guanine, cytosine, uracil and thymine, which may be substituted with a variety of known modifications, such as methyl, amine, halide (e.g. 5-fluorouracil), etc., and a pentose (including ribose and deoxyribose), which may also be substituted with a variety of known modifications, such as amine, o-methyl ester, 2'-deoxy, etc. The nucleotide may also comprise a nucleotide analog which functions as a substrate of the target polymerase, such as acyclovir, gangcyclovir, zidovudine (AZT), etc.

The NTP comprises one or two γ-phosphate phosphoester-linked functional groups (i.e. mono phosphoester or phosphodiesters), providing a functionality such as enhancement of reaction product detectability, cell delivery, polymerase specificity, etc. and/or a reaction product functionality such as a therapeutic or protherapeutic, which functionalities may be provided by a wide variety of structural moieties. Numerous exemplary suitable functional groups are disclosed herein and/or readily identified in convenient screens, such as the polymerase, targeting and specificity screens described below.

In one embodiment, the functional group is a detectable label such as a chromogenic or luminogenic (including fluorogenic) label. In this embodiment, the method generally further comprises, after the incubating step, the step of detecting the label. Accordingly, this aspect of the invention provides safe, simple, efficient, nonradioactive, quantitative assays to detect nucleic acid (RNA and DNA) synthesis by polymerases. The methods need not require a separation step where the substrate does not absorb at the detection wavelength until after it is used in a polymerase reaction. Detection can be effected with conventional spectrophoto/fluorimeters routinely used in research laboratories and classrooms. The methods provide real-time colorimetric assays that easily and efficiently detect and quantify DNA and RNA synthesis.

Chromo/luminogenic NTP analogs offer many advantages to traditional assays that use radioisotopes. They are inexpensive to produce, are stable in the presence of plasma, can be detected with high sensitivity, with a multi-fold signal to background ratio, e.g. at least 7-fold. Furthermore, the assay can be monitored continuously and will give clearly distinguishable results in short time-frames, e.g. within 15 minutes. These assays are readily adapted to a 96-well plate format and performed in commercial ELISA plate readers.

The colorimetric nucleotide analogs are easily detected with normal laboratory equipment. The ability to have individual nucleotides tagged with different chromophores is particularly useful in assays where it is important to analyze substrate specificity. Accordingly, a wide variety of attached chromophores that absorb and emit at different wavelengths may be used. However, for less processive polymerases, an increased sensitivity for detection is advantageous. The coupling of fluorescent analogs to the nucleoside triphosphates increases the sensitivity of detection several-fold. For example, the fluorescent umbelliferone-GTP, is synthesized using the same one-step protocol for the synthesis of PNP-NTPs described herein. The umbelliferone serves as a nucleophile to modify the γ-phosphate. After the polymerase releases umbelliferone-pyrophosphate, alkaline phosphatase removes the phosphates, causing umbelliferone to fluoresce a bright blue color in the presence of UV light.

The invention provides kits for assaying polymerase reactions in standard laboratory spectrophotometers. The kits are designed so that the researcher can replace one or more components with the sample they wish to test. An exemplary kit contains the following components, all supplied at 10×the final concentration:

polymerase substrates including the colorimetric analog;
reaction buffer;
a nucleic acid template suitable for the polymerase;
a nucleic acid template not capable of directing polynucleotide synthesis, a negative control;
polymerase for positive control;
alkaline phosphatase; and
a reaction termination mix.

Exemplary label functionalities shown to be effective in the subject methods are shown in Table 1A; exemplary functionalized NTPs are shown in Table 1B.

TABLE 1A

Exemplary detectable label functionalities.

| | |
|---|---|
| 4-aminophenol | 6-aminonaphthol |
| 4-nitrophenol | 6-nitronaphthol |
| 4-methylphenol | 6-chloronaphthol |
| 4-methoxyphenol | 6-bromonaphthol |
| 4-chlorophenol | 6-iodonaphthol |
| 4-bromophenol | 4,4'-dihydroxybiphenyl |
| 4-iodophenol | 8-hydroxyquinoline |
| 4-nitronaphthol | 3-hydroxypyridine |
| 4-aminonaphthol | umbelliferone |
| 4-methylnaphthol | resorufin |
| 4-methoxynaphthol | 8-hydroxypyrene |
| 4-chloronaphthol | 9-hydroxyanthracene |
| 4-bromonaphthol | 6-nitro9-hydroxyanthracene |
| 4-iodonaphthol | 3-hydroxyflavone |
| 6-methylnaphthol | fluorescein |
| 6-methoxynaphthol | 3-hydroxybenzoflavone |

TABLE 1B

Exemplary labeled NTPs

Adenosine-5'-(γ-4-nitrophenyl)triphosphate
Guanosine-5'-(γ-4-nitrophenyl)triphosphate
Cytosine-5'-(γ-4-nitrophenyl)triphosphate
Thymidine-5'-(γ-4-nitrophenyl)triphosphate
Uracil-5'-(γ-4-nitrophenyl)triphosphate
3'-azido-3'-deoxythymidine-5'-(γ-4-nitrophenyl)triphosphate
3'-azido-2',3'-dideoxythymidine-5'-(γ-4-nitrophenyl)triphosphate
2',3'-didehydro-2',3'-dideoxythymidine-5'-(γ-4-nitrophenyl)triphosphate
Adenosine-5'-(γ-4-aminophenyl)triphosphate
Adenosine-5'-(γ-4-methylphenyl)triphosphate
Adenosine-5'-(γ-4-methoxyphenyl)triphosphate
Adenosine-5'-(γ-4-chlorophenyl)triphosphate
Adenosine-5'-(γ-4-bromophenyl)triphosphate
Adenosine-5'-(γ-4-iodophenyl)triphosphate
Adenosine-5'-(γ-4-nitronaphthyl)triphosphate
Adenosine-5'-(γ-4-aminonaphthyl)triphosphate
Adenosine-5'-(γ-4-methylnaphthyl)triphosphate
Adenosine-5'-(γ-4-methoxynaphthyl)triphosphate
Adenosine-5'-(γ-4-chloronaphthyl)triphosphate
Adenosine-5'-(γ-4-bromonaphthyl)triphosphate
Adenosine-5'-(γ-4-iodonaphthyl)triphosphate
Adenosine-5'-(γ-6-methylnaphthyl)triphosphate
Adenosine-5'-(γ-6-methoxynaphthyl)triphosphate
Adenosine-5'-(γ-6-aminonaphthyl)triphosphate
Adenosine-5'-(γ-6-nitronaphthyl triphosphate
Adenosine-5'-(γ-6-chloronaphthyl)triphosphate
Adenosine-5'-(γ-6-bromonaphthyl)triphosphate
Adenosine-5'-(γ-6-iodonaphthyl)triphosphate
Adenosine-5'-(γ-4'-hydroxybiphenyl)triphosphate
Adenosine-5'-(γ-8-quinolyl)triphosphate
Adenosine-5'-(γ-3-pyridyl)triphosphate
Adenosine-5'-(γ-umbelliferone)triphosphate
Adenosine-5'-(γ-resorufin)triphosphate
Adenosine-5'-(γ-pyrene)triphosphate
Adenosine-5'-(γ-anthracene)triphosphate
Adenosine-5'-(γ-6-nitroanthracene)triphosphate
Adenosine-5'-(γ-flavonyl)triphosphate
Adenosine-5'-(γ-fluorescein)triphosphate
Adenosine-5'-(γ-benzoflavone)triphosphate
Adenosine-5'-(γ-(4-nitrophenyl)-γ'-(4-aminophenyl)triphosphate
Adenosine-5'-(γ-(4-nitrophenyl)-γ'-(4-nitronaphthyl)triphosphate In other embodiments of the invention, the functional group is a predetermined cell delivery enhancing and/or polymerase specificity enhancing moiety, —OR, wherein R is independently selected from substituted or unsubstituted (C1–C18) alkyl, alkenyl, alkynyl and aryl, each inclusive of carbocyclic and heterocyclic. These embodiments relate to nucleotide analogs that provide improved bioavailability and/or cellular uptake (e.g. through enhanced gut or blood stability, cellular and/or membrane permeability, host phosphatase stability, etc.) and/or selectivity, which are extremely important in nucleoside-based therapies. In a particular embodiment, the NTP provides specificity for a pathogenic polymerase, for example, overactive endogenous polymerases of neoproliferative cells and pathogenic bacterial, fungal and viral polymerases. Exemplary targetable bacterial polymerase sources include staphylococcus, exemplary fungal polymerase sources include candida; and exemplary viral polymerase sources include hepatitis viruses including HBV, HAV and HCV, rhinoviruses, influenza, hemorrhagic fever virus, HIV, etc.

For example, nucleoside analogs including AZT and acyclovir are among the most effective antiviral agents in current clinical use. Incorporation of nucleosides lacking a 3' hydroxyl group into a viral nucleic acid prevent additional cycles of nucleotide addition and thereby inhibit the infection process. However, there are two significant drawbacks with this methodology: first, to function as a substrate for a polymerase, a nucleoside must be converted to a triphosphate. Because triphosphates are inherently unstable in an intercellular environment, they cannot be directly administered. Instead, the nucleoside is used as a prodrug, which is converted to a triphosphate via the familiar kinase-catalyzed steps shown below. Thus, for a compound to function as a drug, it must serve as a substrate in three separate phosphorylation steps in addition to serving as a substrate for the targeted polymerase. This is a relatively inefficient process, requiring antiviral nucleosides to be administered in high concentrations. Second, for an antiviral nucleoside to be effective, it must be a substrate for the target polymerase (and the kinases necessary to convert the molecule to a triphosphate), but not inhibit or deactivate cellular processes. Since many host enzymes use nucleoside triphosphates for essential biochemical processes, it has proven difficult to avoid host toxicity. Similar problems occur in many antifungal therapies. For example, flucytosine (5-fluorocytosine) is deaminated to 5-fluorouracil by pathogenic fungi, which can be subsequently metabolized to 5-fluorouridine triphosphate and incorporated into nascent RNA.

Our invention provides new strategies to overcome these problems associated with using nucleosides as therapeutic agents. We have found that attachment to the γ-phosphate of a nucleoside triphosphate of moieties which enhance cell delivery need not preclude its ability to function as a polymerase substrate. Furthermore, such modifications can provide the nucleoside triphosphate relatively enhanced stability toward degradation in serum and provide improved cellular uptake thus improving the potency of known antiviral nucleoside therapeutics by eliminating the need for these compounds to function as kinase substrates. Additionally, antiviral nucleosides that fail in-vivo because they are poor kinase substrates may become therapeutically effective when delivered as modified triphosphates. Furthermore, by increasing pathogen polymerase specificity, we can reduce the toxicity of these molecules toward the host.

Suitable cell delivery enhancing or polymerase specificity enhancing moieties are readily identified empirically. In particular, we generated libraries of modified nucleosides to screen in high throughput for polymerase-specific and cell delivery enhancing modifications. For example, in a particular screen, we use the one step synthesis described herein adapted to standard solid phase methods for parallel array synthesis, to generate moderate sized libraries of 1,000 modified triphosphates. In these syntheses, the resin bound triphosphates are the same, the only variable being the added alcohol. The nucleoside-resin linkage is adapted to the particular base, e.g. resin linkage via the amino functionality of the base in the case of guanine, and the imino function in the case of thymine.

Initial screens concentrated on two modified nucleosides as shown below.

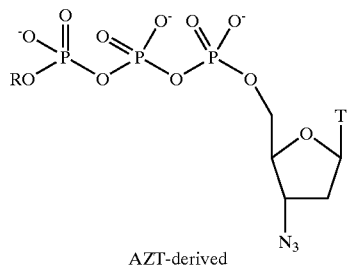

AZT-derived

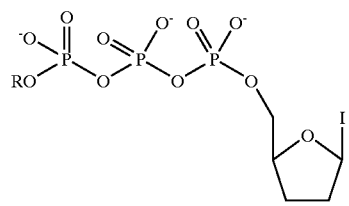

Dideoxy Inosine-derived

The triphosphate libraries are derived from AZT and dideoxyinosine (ddI, Bristol-Meyers Squibb, New York, N.Y.). These are tested against a panel of retroviral polymerases including eleven different HIV reverse transcriptase variants, as well as against human DNA polymerase. Compounds with highest activity against one or more viral targets and lowest activity against the human polymerase are selected for cell-based assays, such as cell penetration screens. To improve cellular penetration, the triphosphate group may be masked as the mixed acetal, as shown below. These uncharged molecules provide enhanced diffusion into cells, where they are subsequently unmasked by endogenous cellular esterases.

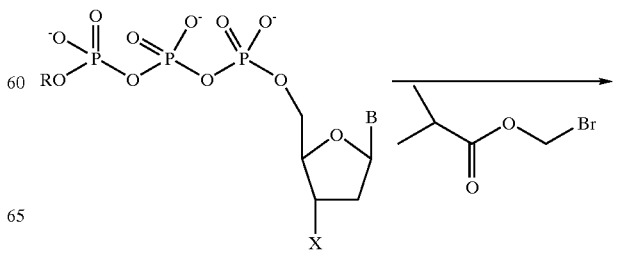

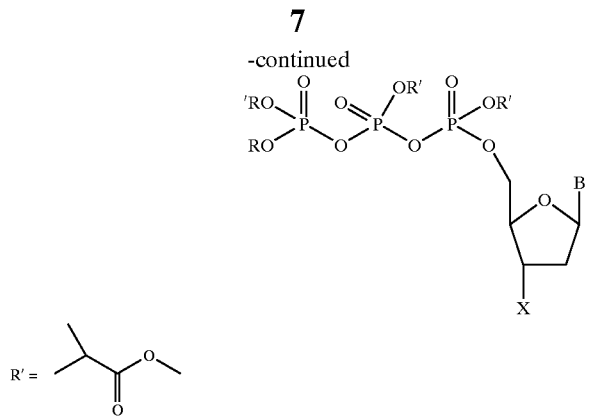

Cell permeant, viral specific compounds may be subsequently modified with a colormnetric or fluorimetric label as described above for reverse transcriptase activity assays.

Cell delivery enhancing moieties encompass a wide variety of generally membrane permeant, relatively hydrophobic R substituents. Exemplary substituted or unsubstituted (C1–C18) alkyl, inclusive of carbocyclic and heterocyclic, cell delivery enhancing functionalities shown to be effective in the subject methods are shown in Table 2A; exemplary functionalized alkyl NTPs are shown in Table 2B. Exemplary substituted or unsubstituted (C1–C18) alkenyl, inclusive of carbocyclic and heterocyclic, cell delivery enhancing functionalities shown to be effective in the subject methods are shown in Table 3A; exemplary functionalized alkenyl NTPs are shown in Table 3B. Exemplary substituted or unsubstituted (C1–C18) alkynyl, inclusive of carbocyclic and heterocyclic, cell delivery enhancing functionalities shown to be effective in the subject methods are shown in Table 5A; exemplary functionalized alkynyl NTPs are shown in Table 4B. Exemplary substituted or unsubstituted (C1–C18) aryl, inclusive of carbocyclic and heterocyclic, cell delivery enhancing functionalities shown to be effective in the subject methods are shown in Table 5A; exemplary functionalized aryl NTPs are shown in Table 5B.

TABLE 2A

Exemplary cell delivery enhancing alkyl functionalities.

| | |
|---|---|
| Methanol | 1-acetoxymethanol(CH$_3$OOCCH$_2$—O—NTP) |
| Ethanol | 2-acetoxyethanol |
| Propanol | 3-acetoxypropanol |
| Butanol | 4-acetoxybutanol |
| Hexanol | 5-acetoxypentanol |
| Octanol | 6-acetoxyhexanol |
| Decanol | 2-nitroethanol |
| Dodecanol | 3-nitropropanol |
| Isopropanol | 4-nitrobutanol |
| Tert-butanol | 5-nitropentanol |
| Cyclohexanol | 5-nitrohexanol |

TABLE 2B

Exemplary cell delivery enhancing alkyl NTPs.

Adenosine-5'-(γ-methyl)triphosphate
Guanosine-5'-(γ-methyl)triphosphate
Cytosine-5'-(γ-methyl)triphosphate
Thymidine-5'-(γ-methyl)triphosphate
Uracil-5'-(γ-methyl)triphosphate
3'-azido-3'-deoxythymidine-5'-(γ-methyl)triphosphate
3'-azido-2',3'-dideoxythymidine-5'-(γ-methyl)triphosphate
2',3'-didehydro-2',3'-dideoxythymidine-5'-(γ-methyl)triphosphate
Adenosine-5'-(γ-ethyl)triphosphate

TABLE 2B-continued

Exemplary cell delivery enhancing alkyl NTPs.

Adenosine-5'-(γ-propyl)triphosphate
Adenosine-5'-(γ-4-butyl)triphosphate
Adenosine-5'-(γ-hexyl)triphosphate
Adenosine-5'-(γ-octyl)triphosphate
Adenosine-5'-(γ-decyl)triphosphate
Adenosine-5'-(γ-dodecyl)triphosphate
Adenosine-5'-(γ-isopropyl)triphosphate
Adenosine-5'-(γ-tert-butyl)triphosphate
Adenosine-5'-(γ-cyclohexyl)triphosphate
Adenosine-5'-(γ-acetoxypropyl)triphosphate
Adenosine-5'-(γ-acetoxymethyl)triphosphate(CH$_3$OOCCH$_2$—O—NTP)
Adenosine-5'-(γ-acetoxyethyl)triphosphate
Adenosine-5'-(γ-acetoxybutyl)triphosphate
Adenosine-5'-(γ-acetoxypentyl)triphosphate
Adenosine-5'-(γ-acetoxyhexyl)triphosphate
Adenosine-5'-(γ-2-nitroethyl)triphosphate
Adenosine-5'-(γ-3-nitropropyl)triphosphate
Adenosine-5'-(γ-4-nitrobutyl)triphosphate
Adenosine-5'-(γ-5-nitropentyl)triphosphate
Adenosine-5'-(γ-methyl)-(γ'-ethyl)triphosphate
Adenosine-5'-(γ-methyl)-(γ'-propyl)triphosphate

TABLE 3A

Exemplary cell delivery enhancing alkenyl functionalities.

| | |
|---|---|
| 1-hydroxy-3-propene | 1-hydroxy-2-cyclohexene |
| 1-hydroxy-4-butene | 1-hydroxy-3-propaldehyde |
| 1-hydroxy-5-pentene | 1-hydroxy-4-butanaldehyde |
| 1-hydroxy-6-hexene | 1-hydroxy-3-Butanone |

TABLE 3B

Exemplary cell delivery enhancing alkenyl NTPs.

Adenosine-5'-(γ-2-propenyl)triphosphate
Guanosine-5'-(γ-2-propenyl)triphosphate
Cytosine-5'-(γ-2-propenyl)triphosphate
Thymidine-5'-(γ-2-propenyl)triphosphate
Uracil-5'-(γ-2-propenyl)triphosphate
3'-azido-3'-deoxythymidine-5'-(γ-2-propenyl)triphosphate
3'-azido-2',3'-dideoxythymidine-5'-(γ-2-propenyl)triphosphate
2',3'-didehydro-2',3'-dideoxythymidine-5'-(γ-2-propenyl)triphosphate
Adenosine-5'-(γ-3-butenyl)triphosphate
Adenosine-5'-(γ-4-pentenyl)triphosphate
Adenosine-5'-(γ-5-hexenyl)triphosphate
Adenosine-5'-(γ-cyclohexenyl)triphosphate
Adenosine-5'-(γ-3-propanaldehyde)triphosphate
[001b]Adenosine-5'-(γ-4-butanaldehyde)triphosphate
Adenosine-5'-(γ-3-butanone)triphosphate

TABLE 4A

Exemplary cell delivery enhancing alkynyl functionalities.

| | |
|---|---|
| 1-hydroxy-2-propyne | 1-hydroxy-4-pentyne |
| 1-hydroxy-3-butyne | 1-hydroxy-5-hexyne |

TABLE 4B

Exemplary cell delivery enhancing alkynyl NTPs.

Adenosine-5'-(γ-2-propynyl)triphosphate
Guanosine-5'-(γ-2-propynyl)triphosphate
Cytosine-5'-(γ-2-propynyl)triphosphate
Thymidine-5'-(γ-2-propynyl)triphosphate
Uracil-5'-(γ-2-propynyl)triphosphate
3'-azido-3'-deoxythymidine-5'-(γ-2-propynyl)triphosphate

TABLE 4B-continued

Exemplary cell delivery enhancing alkynyl NTPs.

3'-azido-2',3'-dideoxythymidine-5'-(γ-2-propynyl)triphosphate
2',3'-didehydro-2',3'-dideoxythymidine-5'-(γ-2-propynyl)triphosphate
Adenosine-5'-(γ-3-butynyl)triphosphate
Adenosine-5'-(γ-4-pentynyl)triphosphate
Adenosine-5'-(γ-5-pentynyl)triphosphate

TABLE 5A

Exemplary cell delivery enhancing aryl functionalities.

| | |
|---|---|
| Phenol | 4-methyl-3-hydroxypyridine |
| 4-Carboxyphenol | 5-methoxy-3-hydroxypyridine |
| 4-Acetoxymethylphenol | 5-nitro-3-hydroxypyridine |
| 4-nitrophenol | 5-acetoxymethyl-3-hydroxypyridine |
| 4-methylphenol | 6-methyl-8-hydroxyquinoline |
| 4-methoxyphenol | 6-methoxy-8-hydroxyquinoline |
| 4-ethylphenol | 4-methyl-8-hydroxyquinoline |
| 4-butylphenol | 6-nitro-8-hydroxyquinoline |
| naphthol | 4-acetoxymethyl-8-hydroxyquinoline |
| 4 or 6 or 8 methylnaphthol | pyrene |
| 4 or 6 or 8 methoxynaphthol | 6-methyl-8-hydroxypyrene |
| 4 or 6 or 8 nitronaphthol | 6-ethyl-8-hydroxypyrene |
| 4 or 6 or 8 ethylnaphthol | 6-nitro-8-hydroxypyrene |
| 4 or 6 or 8 butylnaphthol | 6-(carboxysuccinimidylester)fluorescein |
| 4 or 6 or 8 acetoxymethyl-naphthol | 6-carboxymethyl-2,7-dichlorofluorescein |

TABLE 5B

Exemplary cell delivery enhancing aryl NTPs.

Adenosine-5'-(γ-4-phenyl)triphosphate
Guanosine-5'-(γ-4-phenyl)triphosphate
Cytosine-5'-(γ-4-phenyl)triphosphate
Thymidine-5'-(γ-4-phenyl)triphosphate
Uracil-5'-(γ-4-phenyl)triphosphate
3'-azido-3'-deoxythymidine-5'-(γ-4-phenyl)triphosphate
3'-azido-2',3'-dideoxythymidine-5'-(γ-4-phenyl)triphosphate
2',3'-didehydro-2',3'-dideoxythymidine-5'-(γ-4-phenyl)triphosphate
Adenosine-5'-(γ-4-carboxyphenyl)triphosphate
Adenosine-5'-(γ-(4-acetoxymethyl)phenyl)triphosphate
Adenosine-5'-(γ-4-nitrophenyl)triphosphate
Adenosine-5'-(γ-4-methylphenyl)triphosphate
Adenosine-5'-(γ-4-methoxypheny)triphosphate
Adenosine-5'-(γ-4-ethylphenyl)triphosphate
Adenosine-5'-(γ-4-butylphenyl)triphosphate
Adenosine-5'-(γ-naphthyl)triphosphate
Adenosine-5'-(γ-(4 or 6 or 8 methyl naphthyl)triphosphate
Adenosine-5'-(γ-(4 or 6 or 8 methoxynaphthyl)triphosphate
Adenosine-5'-(γ-(4 or 6 or 8 nitro naphthyl)triphosphate
Adenosine-5'-(γ-(4 or 6 or 8 ethyl naphthyl)triphosphate
Adenosine-5'-(γ-(4 or 6 or 8 butyl naphthyl)triphosphate
Adenosine-5'-(γ-(4 or 6 or 8 acetoxymethyl naphthyl)triphosphate
Adenosine-5'-(γ-(4-methylpyridyl)triphosphate
Adenosine-5'-(γ-(5-methoxypyridyl)triphosphate
Adenosine-5'-(γ-(5-nitropyridyl)triphosphate
Adenosine-5'-(γ-(5-acetoxymethylpyridyl)triphosphate
Adenosine-5'-(γ-(6-methyl-1-quinolyl)triphosphate
Adenosine-5'-(γ-(6-methoxy-1-quinolyl)triphosphate
Adenosine-5'-(γ-(4-methyl-1-quinolyl)triphosphate
Adenosine-5'-(γ-(6-nitro-1-quinolyl)triphosphate
Adenosine-5'-(γ-(4-acetoxymethylpyrenyl)triphosphate
Adenosine-5'-(γ-(6-methylpyrenyl)triphosphate
Adenosine-5'-(γ-(6-ethylpyreny)triphosphate
Adenosine-5'-(γ-(6-nitropyrenyl)triphosphate
Adenosine-5'-(γ-6-(carboxysuccinimidyl fluorescein)triphosphate
Adenosine-5'-(γ-6-carboxymethyl-2,7-dichlorofluorescein)triphosphate
Adenosine-5'-(γ-4-phenyl)-(γ'-4-nitrophenyl)triphosphate
Adenosine-5'-(γ-4-phenyl)-(γ'-4-aminophenyl)triphosphate Polymerase specificity enhancing moieties are readily identified in comparative and competitive enzyme assays. Exemplary substituted or unsubstituted (C1–C18) alkyl, inclusive of carbocyclic and heterocyclic, polymerase specificity enhancing functionalities shown to be effective in the subject methods are shown in Table 6A; exemplary functionalized alkyl NTPs are shown in Table 6B. Exemplary substituted or unsubstituted (C1–C18) alkenyl, inclusive of carbocyclic and heterocyclic, polymerase specificity enhancing functionalities shown to be effective in the subject methods are shown in Table 7A; exemplary functionalized alkenyl NTPs are shown in Table 7B. Exemplary substituted or unsubstituted (C1–C18) alkynyl, inclusive of carbocyclic and heterocyclic, polymerase specificity enhancing functionalities shown to be effective in the subject methods are shown in Table 8A; exemplary functionalized alkynyl NTPs are shown in Table 8B. Exemplary substituted or unsubstituted (C1–C18) aryl, inclusive of carbocyclic and heterocyclic, polymerase specificity enhancing functionalities shown to be effective in the subject methods are shown in Table 9A; exemplary functionalized aryl NTPs are shown in Table 9B.

TABLE 6A

Exemplary polymerase specificity enhancing alkyl functionalities.

| | |
|---|---|
| Methanol | Cyclohexanol |
| Ethanol | 2-carboxy ethanol |
| Propanol | 3-carboxypropanol |
| Butanol | 4-carboxybutanol |
| Hexanol | 2-hydroxyethanol |
| Isopropanol | 3-hydroxypropanol |
| Tert-butanol | 4-hydroxybutanol |
| 2-aminoethanol | 2-nitroethanol |
| 3-aminopropanol | 3-nitropropanol |
| 4-aminobutanol | 4-nitrobutanol |

TABLE 6B

Exemplary polymerase specificity enhancing alkyl NTPs.

Adenosine-5'-(γ-methyl)triphosphate
Guanosine-5'-(γ-methyl)triphosphate
Cytosine-5'-(γ-methyl)triphosphate
Thymidine-5'-(γ-methyl)triphosphate
Uracil-5'-(γ-methyl)triphosphate
3'-azido-3'-deoxythymidine-5'-(γ-methyl)triphosphate
3'-azido-2',3'-dideoxythymidine-5'-(γ-methyl)triphosphate
2',3'-didehydro-2',3'-dideoxythymidine-5'-(γ-methyl)triphosphate
Adenosine-5'-(γ-ethyl)triphosphate
Adenosine-5'-(γ-propyl)triphosphate
Adenosine-5'-(γ-4-butyl)triphosphate
Adenosine-5'-(γ-hexyl)triphosphate
Adenosine-5'-(γ-isopropyl)triphosphate
Adenosine-5'-(γ-tert-butyl)triphosphate
Adenosine-5'-(γ-cyclohexyl)triphosphate
Adenosine-5'-(γ-2-aminoethyl)triphosphate
Adenosine-5'-(γ-3-aminopropyl)triphosphate
Adenosine-5'-(γ-4-aminobutyl)triphosphate
Adenosine-5'-(γ-cyclohexyl)triphosphate
Adenosine-5'-(γ-2-carboxyethyl)triphosphate
Adenosine-5'-(γ-3-carboxypropyl)triphosphate
Adenosine-5'-(γ-4-carboxybutyl)triphosphate
Adenosine-5'-(γ-2-hydroxyethyl)triphosphate
Adenosine-5'-(γ-3-hydroxypropyl)triphosphate
Adenosine-5'-(γ-4-hydroxybutyl)triphosphate
Adenosine-5'-(γ-2-nitroethyl)triphosphate
Adenosine-5'-(γ-3-nitropropyl)triphosphate
Adenosine-5'-(γ-4-nitrobutyl)triphosphate
Adenosine-5'-(γ-methyl)-(g'-ethyl)triphosphate
Adenosine-5'-(γ-methyl)-(γ'-propyl)triphosphate

TABLE 7A

Exemplary polymerase specificity enhancing alkenyl functionalities.

| | |
|---|---|
| 1-hydroxy-2-propene | 1-hydroxy-propaldehyde |
| 1-hydroxy-3-butene | 1-hydroxy-butanaldehyde |
| 1-hydroxy-4-pentene | 1-hydroxy-2-ethylmethylketone |
| 1-hydroxy-5-hexene | 1-hydroxy-butanone |
| 3-cyclohexenol | 1-hydroxy-propanone |

TABLE 7B

Exemplary polymerase specificity enhancing alkenyl NTPs.

Adenosine-5'-(γ-2-propenyl)triphosphate
Guanosine-5'-(γ-2-propenyl)triphosphate
Cytosine-5'-(γ-2-propenyl)triphosphate
Thymidine-5'-(γ-2-propenyl)triphosphate
Uracil-5'-(γ-2-propenyl)triphosphate
3'-azido-3'-deoxythymidine-5'-(γ-2-propenyl)triphosphate
3'-azido-2',3'-dideoxythymidine-5'-(γ-2-propenyl)triphosphate
2',3'-didehydro-2',3'-dideoxythymidine-5'-(γ-2-propenyl)triphosphate
Adenosine-5'-(γ-3-butenyl)triphosphate
Adenosine-5'-(γ-4-pentenyl)triphosphate
Adenosine-5'-(γ-5-hexenyl)triphosphate
Adenosine-5'-(γ-3-cyclohexenyl)triphosphate
Adenosine-5'-(γ-3-propanaldehyde)triphosphate
Adenosine-5'-(γ-4-butanaldehyde)triphosphate
Adenosine-5'-(γ-3-butanone)triphosphate
Adenosine-5'-(γ-3-pentanone)triphosphate

TABLE 8A

Exemplary polymerase specificity enhancing alkynyl functionalities.

| | |
|---|---|
| 1-hydroxy-Propyne | 1-hydroxy-4-pentyne |
| 1-hydroxy-3-butyne | 1-hydroxy-5-hexyne |

TABLE 8B

Exemplary polymerase specificity enhancing alkynyl NTPs.

| | |
|---|---|
| Adenosine-5'-(γ-2-propynyl) triphosphate | 3'-azido-2',3'-dideoxythymidine-5'-(γ-2-propynyl) triphosphate |
| Guanosine-5'-(γ-2-propynyl) triphosphate | 2',3'-didehydro-2',3'-dideoxythymidine-5'-(γ-2-propynyl) triphosphate |
| Cytosine-5'-(γ-2-propynyl) triphosphate | Adenosine-5'-(γ-3-butynyl) triphosphate |
| Thymidine-5'-(γ-2-propynyl) triphosphate | Adenosine-5'-(γ-4-pentynyl) triphosphate |
| Uracil-5'-(γ-2-propynyl) triphosphate | Adenosine-5'-(γ-5-hexynyl) triphosphate |
| 3'-azido-3'-deoxythymidine-5'-(γ-2-propynyl) triphosphate | |

TABLE 9A

Exemplary polymerase specificity enhancing aryl functionalities.

| | |
|---|---|
| Phenol | 4 or 6 or 8 methylnaphthol |
| 4-Carboxyphenol | 4 or 6 or 8 methoxynaphthol |
| 4-methylphenol | 4 or 6 or 8 nitronaphthol |
| 4-methoxyphenol | 4 or 6 or 8 ethylnaphthol |
| 4-nitrophenol | 4 or 6 or 8 butylnaphthol |
| 4-ethylphenol | 4-methyl-3-hydroxypyridine |
| 4-butylphenol | 5-methoxy-3-hydroxypyridine |
| 4-chlorophenol | 5-nitro-3-hydroxypyridine |
| 4-bromophenol | 5-carboxy-3-hydroxypyridine |
| 4-iodophenol | 6-methyl-8-hydroxyquinoline |
| 4-sulfophenol | 6-methoxy-8-hydroxyquinoline |

TABLE 9A-continued

Exemplary polymerase specificity enhancing aryl functionalities.

| | |
|---|---|
| naphthol | 4-methyl-8-hydroxyquinoline |
| | 6-nitro-8-hydroxyquinoline |

TABLE 9B

Exemplary polymerase specificity enhancing aryl NTPs.

| | |
|---|---|
| Adenosine-5'-(γ-4-phenyl) triphosphate | Adenosine-5'-(γ-(4 or 6 or 8 methoxynaphthyl)triphosphate |
| Guanosine-5'-(γ-4-phenyl) triphosphate | Adenosine-5'-(γ-(4 or 6 or 8 nitro naphthyl)triphosphate |
| Cytosine-5'-(γ-4-phenyl) triphosphate | Adenosine-5'-(γ-(4 or 6 or 8 ethyl naphthyl)triphosphate |
| Thymidine-5'-(γ-4-phenyl) triphosphate | Adenosine-5'-(γ-(4 or 6 or 8 butyl naphthyl)triphosphate |
| Uracil-5'-(γ-4-phenyl) triphosphate | Adenosine-5'-(γ-(4-methylpyridyl) triphosphate |
| 3'-azido-3'-deoxythymidine-5'-(γ-4-phenyl) triphosphate | Adenosine-5'-(γ-(5-methoxypyridyl) triphosphate |
| 3'-azido-2',3'-dideoxythymidine-5'-(γ-4-phenyl) triphosphate | Adenosine-5'-(γ-(5-nitropyridyl) triphosphate |
| 2',3'-didehydro-2',3'-dideoxythymidine-5'-(γ-4-phenyl) triphosphate | Adenosine-5'-(γ-(5-carboxypyridyl) triphosphate |
| Adenosine-5'-(γ-4-carboxyphenyl) triphosphate | Adenosine-5'-(γ-(6-methylquinolyl) triphosphate |
| Adenosine-5'-(γ-4-nitrophenyl) triphosphate | Adenosine-5'-(γ-(6-methoxyquinolyl) triphosphate |
| Adenosine-5'-(γ-4-methylphenyl) triphosphate | Adenosine-5'-(γ-(4-methylquinolyl) triphosphate |
| Adenosine-5'-(γ-4-methoxyphenyl) triphosphate | Adenosine-5'-(γ-(6-nitroquinolyl) triphosphate |
| Adenosine-5'-(γ-4-ethylphenyl) triphosphate | Adenosine-5'-(γ-(6-nitroquinolyl)-γ'-(4-nitrophenyl) triphosphate |
| Adenosirie-5'-(γ-4-butylphenyl) triphosphate | Adenosine-5'-(γ-(4-chlorophenyl)-γ'-(4-nitrophenyl) triphosphate |
| Adenosine-5'-(γ-4-chlorophenyl) triphosphate | |
| Adenosine-5'-(γ-4-bromophenyl) triphosphate | |
| Adenosine-5'-(γ-4-iodophenyl) triphosphate | |
| Adenosine-5'-(γ-4-sulfophenyl) triphosphate | |
| Adenosine-5'-(γ-naphthyl) triphosphate | |
| Adenosine-5'-(γ-(4 or 6 or 8 methyl naphthyl)triphosphate | |

In the foregoing and other embodiments of the invention, the functional group may be or also comprise a moiety which upon polymerization of the nucleotide, provides a reaction product functionality such as a therapeutic or pro-therapeutic. A wide variety of bioactive molecules can be coupled to the nucleotide through the γ-phosphoester linkage. After polymerization, the pyrophosphate-linked functionality may be an active form, or may be further hydrolyzed to yield a bioactive or therapeutic molecule. Accordingly, this embodiment may further comprise a subsequent incubation in the presence of one or more phosphatases under conditions wherein the β-γ bond and/or γ-phosphoester bond is cleaved such that the liberated pyrophosphate-linked functionality is converted to the monophosphate and/or the unphosphorylated functionality. In addition, the same moiety may provide a plurality of functionalities, e.g. both cell delivery enhancing and pro-drug functionalities. These functional groups provide particular application in targeting pathogenic polymerases, particularly pathogenic viral polymerases, and encompass a wide variety of hydroxyl-bearing substituents, —OR, wherein R is independently selected from substituted or unsubstituted (C1–C18) alkyl, alkenyl, alkynyl and aryl, each inclusive of carbocyclic and heterocyclic. Suitable moieties may be identified in viremia assays, such as described below, and/or derive from established therapeutics. For example, targetable functionalities include γ-phosphesters of a number of antiviral agents such as amantadine and rimantadine, α, β and γ-interferons, non-nucleoside reverse transcriptase inhibitors such as nevirapine, delaviridine, loviride, etc. and protease inhibitors such as saquinavir, saquinavir mesylate, ritonavir, indinavir, nelfinavir, amprenavir etc. Coupling chemistry is readily selected by those of ordinary skill in accordance with the structure of the targeted functionality. For example, the foregoing peptide mimetic protease inhibitors all provide a single reactive hydroxyl group which is readily coupled to nucleoside triphosphates as outlined below. Exemplary pyrophosphate-prodrug liberating antiviral nucleotides made by these methods are shown in Table 10.

TABLE 10

Exemplary pyrophosphate-prodrug liberating antiviral NTPs.

3'-azido-3'-deoxythymidine-5'-(γ-saquinavir) triphosphate
3'-azido-3'-deoxythymidine-5'-(γ-ritonavir) triphosphate
3'-azido-3'-deoxythymidine-5'-(γ-indinavir) triphosphate
3'-azido-3'-deoxythymidine-5'-(γ-nelfinavir) triphosphate
3'-azido-3'-deoxythymidine-5'-(γ-amprenavir) triphosphate
3'-azido-2',3'-dideoxythymidine-5'-(γ-saquinavir) triphosphate
3'-azido-2',3'-dideoxythymidine-5'-(γ-ritonavir) triphosphate
3'-azido-2',3'-dideoxythymidine-5'-(γ-indinavir) triphosphate
3'-azido-2',3'-dideoxythymidine-5'-(γ-nelfinavir) triphosphate
3'-azido-2',3'-dideoxythymidine-5'-(γ-amprenavir) triphosphate General synthetic scheme: Modifying a nucleoside triphosphate on the terminal phosphoryl group is technically straightforward. This is accomplished by treating the triphosphate tetramethylammonium carbonate with dicyclohexyl carbodiimide (DCC) in DMF to generate the cyclic anhydride (which is not isolated), followed by treatment with a nucleophile (ROH). After the reaction has proceeded for about 20 hours the solvent is evaporated and the solid residue purified to obtain the R-NTP. This strategy is diagramed below.

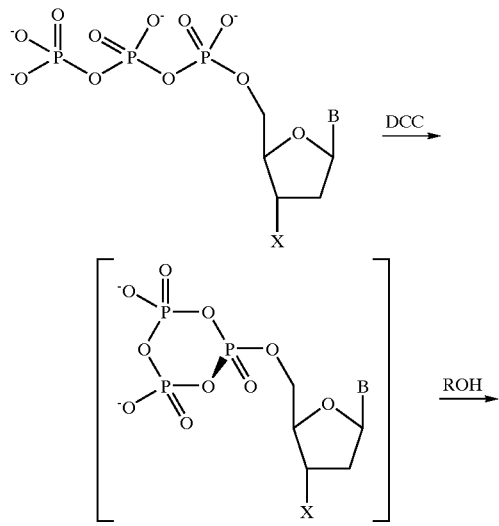

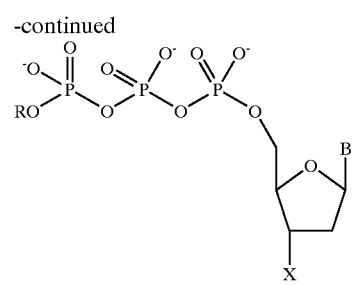

Synthetic scheme for PNP-NTPs: ATP is treated with DCC to generate the cyclic anhydride; and then treated with a nucleophile 4-nitrophenol to give PNP-ATP. GTP is treated with dicyclohexyl carbodiimide (DCC) to generate the cyclic anhydride; and then treated with a nucleophile 4-nitrophenol PNP-GTP. CTP is treated with DCC to generate the cyclic anhydride; and then treated with a nucleophile 4-nitrophenol PNP-CTP. UTP is treated with dicyclohexyl carbodiimide (DCC) to generate the cyclic anhydride; and then treated with a nucleophile 4-nitrophenol PNP-UTP.

EXAMPLES

Example 1

Exemplary methodologies using PNP-NTP analogs. This example provides exemplary methodologies used to demonstrate a particular aspect of the invention.

Production of the PNP-NTP analogs. PNP-GTP and PNP-ATP are made in one high yielding reaction from commercially available starting materials (Scheme 1). When the nucleotide analog is used in RNA synthesis, the β and γ phosphates are released (as pyrophosphate) with the attached PNP. While this compound is colorless, the enzyme alkaline phosphatase rapidly hydrolyzes the pyrophosphates to release PNP, which, at the pH of the polymerase reaction, has a yellow color that absorbs maximally at 405 nM.

Scheme 1
A general scheme for the use of nucleotide analog PNT-NTP to assess polymerase activity

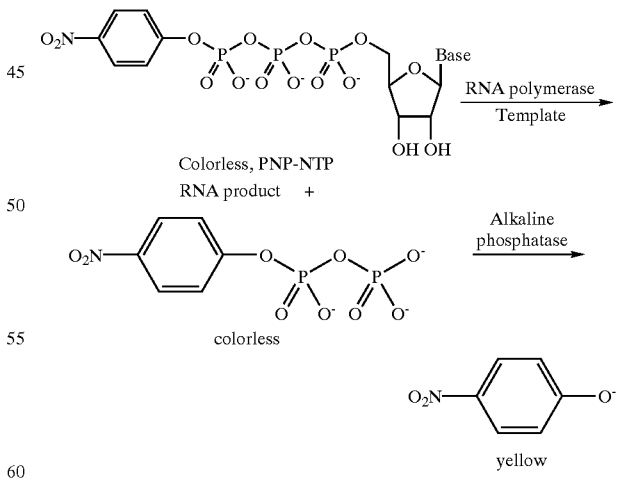

PNP-NTPs were synthesized and purified within a two-day period. The PNP-GTP analog was made by covalently linking the nucleotide with DCC as described herein. The synthesis of PNP-ATP was modified from a previously published protocol (Clare et al., 1993. Euro. J. Biochem. 214, 459). The structures of the molecules were confirmed by nuclear magnetic resonance spectroscopy and the purity was greater than 95%. The overall yield of the synthesis is between 50 and 60% of the starting reagents. We have determined that 60 nmoles of the compound is more than sufficient to direct one polymerase assay. Since $60 of reagents and supplies will yield enough purified PNP-GTP or PNP-ATP for ca. 2000 assays, the cost of raw materials per assay is less than 3 cents. The reaction can be scaled up many-fold without any logistical complications.

PNP-NTPs are useful reporters for the activities of a variety of RNA polymerases. Initial demonstrations showed PNP-GTP is a suitable substrate for T7 DNA-dependent RNA polymerase and the brome mosaic virus RdRp. PNP-GTP used in place of GTP directed RNA synthesis at levels similar to reactions containing normal GTP. A reaction that lacked either PNP-GTP or GTP failed to generate RNA products, as expected. Identical results were observed with the RdRp of bovine viral diarrhea virus, a member of the same family as hepatitis C virus. PNP release was also observed during RNA synthesis by the SP6 RNA polymerase. The presence of a template containing an SP6 promoter and the SP6 polymerase resulted in A405 at 7-fold above background after a one hour incubation. Viral RdRps also reproducibly resulted in PNP release only when the enzyme was presented with a cognate template. All RNA polymerases tested demonstrated the ability to recognize PNP-NTPs in RNA synthesis assays.

PNP-NTPs are useful as continuous reporters for RNA polymerase activity. To simplify the components, transcription reactions were performed in the presence of alkaline phosphatase, a homodeoxycytidylate template that directs the incorporation of only guanylates (named WV-15C), PNP-GTP, and T7 RNA polymerase. The use of homopolymers is well accepted in assessing the activities of viral RNA polymerases, including the HCV RdRp (Lohman et al., 1997. J. Virol., 71, 8416). The reaction was monitored in a spectrometer at 405 nM, the maximum absorbance for PNP. Ten minutes after the start of the reaction, absorbance at levels distinctly above background was observed. This increase in absorbance due to PNP release was linear over a two-hour period, coincident with the increase in RNA polymerase activity. There were several negative controls in this experiment, all of which yielded minimal PNP release: 1) a reaction without T7 RNA polymerase; 2) a reaction that lacked the essential cofactor, $Mg^{2+}$; 3) a reaction that contained homothymidylate (WV-15T), rather than WV-15C. Lastly, a linear increase in absorbance at 405 nm was observed in a transcription reaction with a homothymidylate template and PNP-ATP. In a separate experiment, the amount of PNP release was found to correlate directly with the number of T7 RNA polymerase molecules used in the reaction. These results demonstrate that polymerase activity can be monitored by the release of PNP from either PNP-GTP or PNP-ATP.

The PNP-NTP colorimetric polymerase assay can use non-homopolymeric templates. Transcription reactions were performed with plasmids that either contained a T7 promoter (pBSII KS+) or lacked it (pUC18). Due to the complexity of the template sequence and the need for unblocked NTPs, alkaline phosphatase was added only after a specified polymerization time to prevent the degradation of the NTPs. We find that only the plasmid with a T7 promoter was able to result in an increased absorbance at 405 nm. These results indicate that PNP-NTPs can be used to monitor RNA polymerase activity from a variety of templates.

PNP-NTPs are stable in plasma. The ability to assay for viral polymerase activity in serum or other body fluid would greatly increase the usefulness of this colorimetric polymerase assay. PNP-NTPs were resistant to cellular phosphatases because the incubation of PNP-GTP with alkaline phosphatase, but not T7 RNA polymerase, did not result in PNP release. To test the effect of more complex, biologically relevant mixtures of enzymes on PNP-NTP stability, blood was collected and centrifuged to remove cells and collect the plasma. Incubation of plasma to 10% final volume and PNP-GTP did not increase the absorbance at 405 nm over a 7 h incubation. The presence of alkaline phosphatase, polymerase, and a noncognate template increased PNP levels slightly after 7 hours. However, a complete transcription reaction with a cognate template resulted in absorbance>7 fold higher than background 3 h after the start of the polymerase reaction. Identical trends were observed in reactions that contained PNP-ATP and the WV-15T template. These results clearly demonstrate that the PNP-nucleotide analogs can be used in assays containing plasma.

Example 2

In vitro Reverse Transcription Sssay for Identifying Polymerase Specificity Enhancing dNTPs The reaction mixture (50 µl) contains 50 mM Tris.HCl, pH 7.8, 5 mM dithiothreitol, 300 mM glutathione, 500 µM EDTA, 150 mM KCl, 5 mM $MgCl_2$, 1.25 µg of bovine serum albumin, a fixed concentration of the labeled substrate [2,8-$^3$H]dGTP (2.95 µM, 2 µCi), a fixed concentration of the template/primer poly(C).oligo(dG) (0.1 mM), 0.06% Triton X-100, 5 µl of inhibitor solution [containing various concentrations (5-fold dilutions) of the test compounds], and 5 µl of the RT preparation. The reaction mixtures are incubated at 37° C. for 30 min, at which time 100 µl of calf thymus DNA (150 µg/ml), 2 ml of $Na_4P_2O_7$ (0.1 M in 1M HCl), and 2 ml of trichloroacetic acid (10%, v/v) are added. The solutions are kept on ice for 30 min, after which the acid-insoluble material is washed and analyzed for radioactivity. The $IC_{50}$ of the test compounds is determined as the compound concentration that inhibited the virus particle-derived RT activity by 50%.

TABLE 11

Anti-HIV-1 RT spectrum of different mutant HIV-1 strains against exemplary NTPs (50% inhibitory concentration, IC, µg/ml); substrate: [2,8 $^3$H]dGTP (2.95 µM); template: poly(rC)oligo(dG)

| Compound/<br>Virus | HIV-1/<br>($III_B$)<br>(wild type) | HIV-1/TIBO<br>R82150<br>(100-Ile) | HIV-1/Nev<br>(106-Ala) | HIV-1/<br>TSAO-$m^3$T<br>(138-Lys) | HIV-1/Pyr<br>(181-Cys) |
|---|---|---|---|---|---|
| HRT175 | 0.06 | 0.38 | 0.14 | 0.13 | 0.63 |
| HRT202 | 0.12 | 0.51 | 0.21 | 0.87 | 0.45 |
| HRT405 | 0.05 | 0.25 | 0.19 | 0.23 | 0.39 |
| HRT517 | 0.16 | 0.33 | 0.08 | 0.21 | 0.47 |

TABLE 11-continued

Anti-HIV-1 RT spectrum of different mutant HIV-1
strains against exemplary NTPs (50% inhibitory concentration,
IC, μg/ml); substrate: [2,8 $^3$H]dGTP (2.95 μM);
template: poly(rC)oligo(dG)

| Compound/<br>Virus | HIV-1/<br>(III$_B$)<br>(wild type) | HIV-1/TIBO<br>R82150<br>(100-Ile) | HIV-1/Nev<br>(106-Ala) | HIV-1/<br>TSAO-m$^3$T<br>(138-Lys) | HIV-1/Pyr<br>(181-Cys) |
|---|---|---|---|---|---|
| HRT559 | 0.01 | 0.26 | 0.26 | 0.35 | 0.52 |
| HRT871 | 0.42 | 0.17 | 0.31 | 0.72 | 0.86 |

Example 3
Cell-based Retrovirus Infectivity Inhibition Sssay for Identifying Cell Delivery Enhancing NTPs CEM cells are obtained from the American Tissue Cell Culture Collection (Rockville, Md.). HIV-1(IIIB) is obtained from the culture supernatant of persistently HIV-1-infected H9 cells (R. C. Gallo and M. Popovic, National Institutes of Health, Bethesda, Md.).

Sensitivity of several HIV-1 mutant strains to the test compounds in CEM cell cultures. CEM cells are suspended at 250,000 cells per ml of culture medium and infected with wild-type HIV-I(III$_B$) or mutant HIV-1 strains at 100 50% cell culture infective doses per ml. Then 100 μl of the infected cell suspensions was added to 200 μl microtiter plate wells containing 100 μl of an appropriate dilution of the test compounds. After 4 days incubation at 37° C., the cell cultures were examined for syncytium formation. The 50% effective concentration (EC50) was determined as the compound concentration required to inhibit HIV-1-induced cytopathicity (syncytium formation) in CEM cells by 50%.

Table 12. Sensitivity/Resistance spectrum of different mutant HIV-1 strains against exemplary NTPs (50% effective concentration, EC, μg/ml); mutant virus strains that contain the 100 Leu-Ile, 106 Val-Ala, 138 Glu-Lys or 181 Tyr-Cys mutation in their RT are obtained after selection in cell culture in the presence of TIBO R82150, nevirapine, TSAOm$^3$T and pyridinone L697,661, respectively.

| Compound/<br>Virus | HIV-1/<br>(III$_B$)<br>(wild type) | HIV-1/TIBO<br>R82150<br>(100-Ile) | HIV-1/Nev<br>(106-Ala) | HIV-1/<br>TSAO-m$^3$T<br>(138-Lys) | HIV-1/Pyr<br>(181-Cys) |
|---|---|---|---|---|---|
| HRT175 | 0.04 | 0.11 | 0.08 | <0.05 | 0.16 |
| HRT202 | <0.05 | 0.14 | 0.13 | <0.01 | 0.15 |
| HRT405 | 0.03 | <0.05 | <0.05 | 0.03 | 0.23 |
| HRT517 | 0.06 | 0.18 | <0.05 | 0.07 | 0.37 |
| HRT559 | <0.01 | <0.05 | 0.12 | 0.03 | 0.45 |
| HRT871 | 0.02 | <0.10 | 0.09 | 0.02 | 0.26 |

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for polymerizing a nucleotide comprising the steps of:
    forming a mixture of a polymerase and a nucleoside triphosphate (NTP) comprising α,β and γ phosphates and a γ-phosphate phosphoester-linked functional group; and
    incubating the mixture under conditions wherein the polymerase catalyzes cleavage of the NIP between the α and β phosphates, liberating a pyrophosphate comprising the functional group and polymerizing a resultant nucleoside monophosphate.

2. A method according to claim 1 wherein the functional group is a detectable label and the method further comprises, after the incubating step, the step of detecting the label.

3. A method according to claim 1 wherein the functional group is a detectable label and the method further comprises the step of detecting the label and the label is selected from the group consisting of the compounds of Table 1A.

4. A method according to claim 1, wherein the functional group is a cell delivery enhancing moiety, —OR wherein R is selected from substituted or unsubstituted (C1–C18) alkyl, alkenyl, alkynyl and aryl.

5. A method according to claim 1, wherein the functional group is a cell delivery enhancing moiety, —OR wherein R is substituted or unsubstituted (C1–C18) alkyl.

6. A method according to claim 1, wherein the functional group is a cell delivery enhancing moiety, —OR wherein R is substituted or unsubstituted (C1–C18) alkyl selected from the group consisting of the compounds of Table 2A.

7. A method according to claim 1, wherein the functional group is a cell delivery enhancing moiety, —OR wherein R is substituted or unsubstituted (C1–C18) alkenyl.

8. A method according to claim 1, wherein the functional group is a cell delivery enhancing moiety, —OR wherein R is substituted or unsubstituted (C1–C18) alkenyl selected from the group consisting of the compounds of Table 3A.

9. A method according to claim 1, wherein the functional group is a cell delivery enhancing moiety, —OR wherein R is substituted or unsubstituted (C1–C18) alkynyl.

10. A method according to claim 1, wherein the functional group is a cell delivery enhancing moiety, —OR wherein R is substituted or unsubstituted (C1–C18) alkynyl selected from the group consisting of the compounds of Table 4A.

11. A method according to claim 1, wherein the functional group is a cell delivery enhancing moiety, —OR wherein R is substituted or unsubstituted (C1–C18) aryl.

12. A method according to claim 1, wherein the functional group is a cell delivery enhancing moiety, —OR wherein R is substituted or unsubstituted (C1–C18) aryl selected from the groups consisting of the compounds of Table 5A.

13. A method according to claim 1, wherein the functional group is a polymerase specificity enhancing moiety, —OR wherein R is selected from substituted or unsubstituted (C1–C18) alkyl, alkenyl, alkynyl and aryl.

14. A method according to claim 1, wherein the functional group is a polymerase specificity enhancing moiety, —OR wherein R is substituted or unsubstituted (C1–C18) alkyl.

15. A method according to claim 1, wherein the functional group is a polymerase specificity enhancing moiety, —OR wherein R is substituted or unsubstituted (C1–C18) alkyl selected from the group consisting of the compounds of Table 6A.

16. A method according to claim 1, wherein the functional group is a polymerase specificity enhancing moiety, —OR wherein R is substituted or unsubstituted (C1–C18) alkenyl.

17. A method according to claim 1, wherein the functional group is a polymerase specificity enhancing moiety, —OR wherein R is substituted or unsubstituted (C1–C18) alkenyl selected from the group consisting of the compounds of Table 7A.

18. A method according to claim 1, wherein the functional group is a polymerase specificity enhancing moiety, —OR wherein R is substituted or unsubstituted (C1–C18) alkynyl.

19. A method according to claim 1, wherein the functional group is a polymerase specificity enhancing moiety, —OR wherein R is substituted or unsubstituted (C1–C18) alkynyl selected from the group consisting of the compounds of Table 8A.

20. A method according to claim 1, wherein the functional group is a polymerase specificity enhancing moiety, —OR wherein R is substituted or unsubstituted (C1–C18) aryl.

21. A method according to claim 1, wherein the functional group is a polymerase specificity enhancing moiety, —OR wherein R is substituted or unsubstituted (C1–C18) aryl selected from the group consisting of the compounds of Table 9A.

22. A method according to claim 1, wherein the functional group is a pyrophosphate-prodrug liberating moiety, —OR wherein R is selected from substituted or unsubstituted (C1–C18) alkyl, alkenyl, alkynyl and aryl.

23. A method according to claim 1, wherein the functional group is a a pyrophosphate-prodrug liberating moiety, —OR wherein R is selected from substituted or unsubstituted (C1–C18) alkyl, alkenyl, alkynyl and aryl and selected from the group consisting of the compounds of Table 10.

* * * * *